US009212361B2

(12) United States Patent
Jaisser et al.

(10) Patent No.: US 9,212,361 B2
(45) Date of Patent: Dec. 15, 2015

(54) METHODS AND PHARMACEUTICAL COMPOSITIONS FOR THE TREATMENT OF HYPERTENSION

(71) Applicants: INSERM, Paris (FR); UNIVERSITE PARIS DIDEROT (PARIS VII); UNIVERSITE PARIS DESCARTES, Paris (FR)

(72) Inventors: Frederic Jaisser, Paris (FR); Nicolette Farman, Paris (FR); Antoine Tarjus, Paris (FR)

(73) Assignees: Institut National de la Sante et de la Recherche Medicale (INSERM), Paris (FR); Universite Paris Diderot (Paris VII), Paris (FR); Universite Paris Descartes, Paris (FR)

( * ) Notice: Subject to any disclaimer, the term of this patent is extended or adjusted under 35 U.S.C. 154(b) by 0 days.

(21) Appl. No.: 14/395,080

(22) PCT Filed: Apr. 18, 2013

(86) PCT No.: PCT/IB2013/001172
§ 371 (c)(1),
(2) Date: Oct. 17, 2014

(87) PCT Pub. No.: WO2013/156867
PCT Pub. Date: Oct. 24, 2013

(65) Prior Publication Data
US 2015/0073034 A1 Mar. 12, 2015

(51) Int. Cl.
| | |
|---|---|
| *A61K 48/00* | (2006.01) |
| *C12N 15/113* | (2010.01) |
| *C12N 15/115* | (2010.01) |
| *A61K 31/713* | (2006.01) |
| *G01N 33/50* | (2006.01) |

(52) U.S. Cl.
CPC .......... *C12N 15/113* (2013.01); *A61K 31/713* (2013.01); *C12N 15/115* (2013.01); *G01N 33/502* (2013.01); *G01N 33/5044* (2013.01); *C12N 2310/14* (2013.01); *C12N 2320/10* (2013.01); *C12N 2320/30* (2013.01)

(58) Field of Classification Search
None
See application file for complete search history.

(56) References Cited

U.S. PATENT DOCUMENTS

2004/0132984 A1* 7/2004 Dieckmann et al. ......... 536/23.2
2008/0095782 A1* 4/2008 Xu et al. .................... 424/139.1

FOREIGN PATENT DOCUMENTS

| WO | 2007/028053 A2 | 3/2007 |
| WO | 2009/132510 A1 | 11/2009 |
| WO | 2010/046411 A1 | 4/2010 |
| WO | 2012/072820 A1 | 6/2012 |

OTHER PUBLICATIONS

Rahmouni et al. (Hypertension, 2005; 45:9-14).*
Pitt et al. (JACC 1993, vol. 22: 6A-13A).*
Elbashir et al., "Duplexes of 21-Nucleotide RNAS Mediate RNA Interference in Cultured Mammalian Cells", Nature: International Weekly Journal of Science (and Supplementary Information), May 24, 2001, pp. 494-498, vol. 411, Nature Publishing Group, UK.
Bolignano et al., "Increased plasma neutrophil gelatinase-associate lipocalin levels predict mortality in elderly patients with chronic heart failure", Rejuvenation Research, Mar. 10, 2009, pp. 7-14, vol. 12, No. 1, Mary Ann Liebert, New Rochelle, NY, US.
Latouche et al., "Neutrophil Gelatinase-Associated Lipocalin Is a Novel Mineralocorticoid Target in the Cardiovascular System", Hypertension, Apr. 2, 2012, pp. 966-972, vol. 59, No. 5.
Yndestad et al., "Increased systemic and myocardial expression of neutrophil gelatinase-associated lipocalin in clinical and experimental heart failure", European Heart Journal, May 1, 2009, pp. 1229-1236, vol. 30, No. 10, Oxford University Press, GB.
Limin et al., "Lipocalin-2/Neutrophil Gelatinase-B Associated Lipocalin Is Strongly Induced in Hearts of Rats With Autoimmune Myocarditis and in Human Myocarditis", Circulation Journal, Mar. 1, 2010, pp. 523-530, vol. 74, No. 3, Japanese Circulation Society, Kyoto, JP.
McMurray, "Systolic Heart Failure", New England Journal of Medicine, Jan. 1, 2010, pp. 228-238, vol. 362, No. 3, Massachusetts Medical Society, Waltham, MA, US.

* cited by examiner

*Primary Examiner* — Kimberly Chong
(74) *Attorney, Agent, or Firm* — Whitham Curtis Christofferson & Cook, PC

(57) ABSTRACT

The present invention relates to an inhibitor of Neutrophil Gelatinase-Associated Lipocalin (NGAL) activity or expression for use in a method for treating or preventing hypertension in a subject in need thereof.

3 Claims, 4 Drawing Sheets

METHODS AND PHARMACEUTICAL COMPOSITIONS FOR THE TREATMENT OF HYPERTENSION

FIELD OF THE INVENTION

Figure 1A:
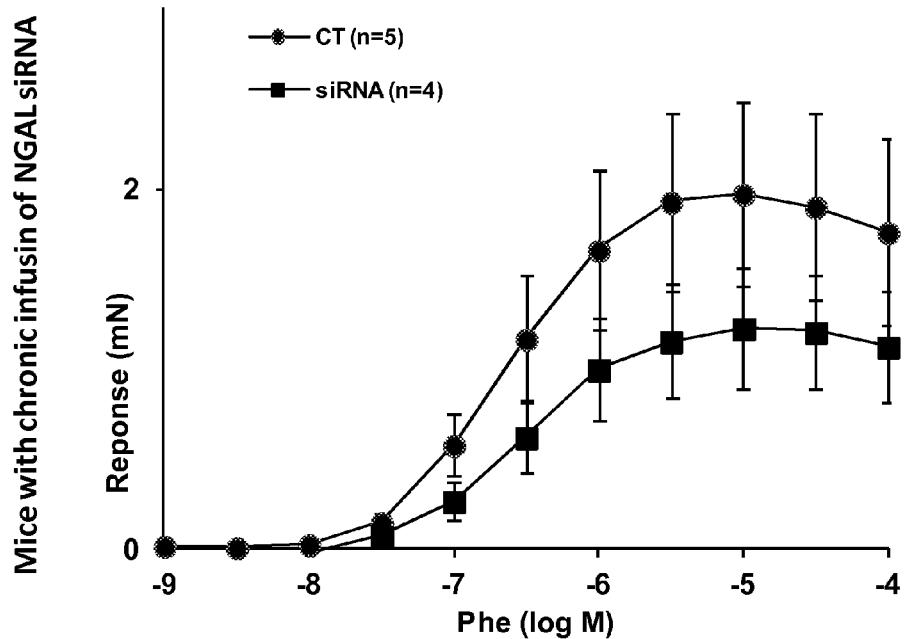

The present invention relates to a methods and pharmaceutical compositions for the treatment of hypertension.

BACKGROUND OF THE INVENTION

Hypertension is the most common risk factor for cardiovascular disease, and is considered as the leading cause of death in many developed countries. Hypertension, the most is usually defined as high blood pressure. A combination of genetic and environmental factors contribute to the development of hypertension. The therapeutic class of antihypertensive drugs comprises calcium channel blocking agents (e.g. Nifedipine (Adalat®, Procardia®), verapamil (Calan®, Isoptin®) and diltiazem (Cardizem®), netrendipine or amlodipine) that, inhibit the movement of ionic calcium across the cell membrane and thus reduces the force of contraction of muscles of the heart and arteries. The class also comprise peripheral vasodilators such as hydralazine (Apresoline®), isoxuprine (Vasodilan®), and minoxidil (Loniten®) that act by relaxing blood vessels. There are also several groups of drugs which act by reducing adrenergic nerve stimulation, the excitatory nerve stimulation that causes contraction of the muscles in the arteries, veins and heart. These drugs include the beta-adrenergic blockers ("beta blockers") and alpha/beta adrenergic blockers. Beta blockers include propranolol (Inderal®), atenolol (Tenomiin®), and pindolol (Visken®). Alpha/beta adrenergic blockers include labetolol (Normodyne®, Trandate®) and carvedilol (Coreg®). Angiotensin-converting enzyme ("ACE") inhibitors act by inhibiting the production of angiotensin II, a substance that both induces constriction of blood vessels and retention of sodium, which leads to water retention and increased blood volume. There are many ACE inhibitors including captopril (Capoten®), benazepril (Lotensin®), enalapril (Vasotec®), and quinapril (Acupril®). The angiotensin II receptor agonists, losartan (Cozaar®), candesartan (Atacand®), irbesartan (Avapro®), telmisartan (Micardis®), valsartan (Diovan®) and eprosartan (Teveten®) directly inhibit the effects of angiotensin II rather than blocking its production (like the ACE inhibitors). In addition to these drugs, other classes of drugs have been used to lower blood pressure, most notably the thiazide diuretics. These include hydrochlorothiazide (Hydrodiuril®, Esidrex®), indapamide (Lozol®), polythiazide (Renese®), and hydroflumethiazide (Diucardin®). However the limited successful treatment of hypertension is limited by a relatively small number of therapeutic targets for blood pressure regulation. The present invention fulfils this need by providing a new therapeutic target for the treatment of hypertension.

SUMMARY OF THE INVENTION

The present invention relates to an inhibitor of Neutrophil Gelatinase-Associated Lipocalin (NGAL) activity or expression for use in a method for treating or preventing hypertension in a subject in need thereof.

DETAILED DESCRIPTION OF THE INVENTION

The present invention relates to an inhibitor of Neutrophil Gelatinase-Associated Lipocalin (NGAL) activity or expression for use in a method for treating or preventing hypertension in a subject in need thereof.

The terms "subject," and "patient," used interchangeably herein, refer to a mammal, particularly a human who has been previously diagnosed with hypertension or who is at risk for having or developing hypertension. Typically, the subject may suffer from any type of hypertension, including arterial hypertension, venous hypertension and pulmonary hypertension. In a particular embodiment, the subject is non obese subject.

In one embodiment, the inhibitor of NGAL activity or expression is particularly suitable for reducing chronic vascular inflammation in a patient suffering from hypertension.

As used herein, the term "NGAL" has its general meaning in the art and refers to the Neutrophil Gelatinase-Associated Lipocalin as described in Schmidt-Ott K M. et al. (2007) (Schmidt-Ott K M, Mori K, Li J Y, Kalandadze A, Cohen D J, Devarajan P, Barasch J. Dual action of neutrophil gelatinase-associated lipocalin. J Am Soc Nephrol. 2007 February; 18(2):407-13. Epub 2007 Jan. 17. Review.). NGAL was shown to exist both as a 25-kDa monomer and a 45-kDa disulfide-linked homodimer, and it may also be covalently complexed with neutrophil gelatinase (also known as matrix metalloproteinase 9, MMP-9) via an intermolecular disulphide bridge as a 135-kDa heterodimeric form.

An "inhibitor of NGAL activity" has its general meaning in the art, and refers to a compound (natural or not) which has the capability of reducing or suppressing the activity of NGAL. For example the compound may block the interaction of NGAL with the NGAL binding ligands, or may bind to NGAL in manner that NGAL losses its capacity to interact with gelatinase, and thus altering gelatinase activity. Typically, said inhibitor is a small organic molecule or a biological molecule (e.g. peptides, lipid, antibody, aptamer . . . ).

In a particular embodiment, the activity of NGAL can be reduced using a "dominant negative." To this end, constructs which encode, for example, defective NGAL polypeptide, can be used in gene therapy approaches to diminish the activity of NGAL on appropriate target cells. For example, nucleotide sequences that direct host cell expression of NGAL in which all or a portion of the DNA binding domain is altered or missing can be administered to the subject (either by in vivo or ex vivo gene therapy methods known in the art). Alternatively, targeted homologous recombination can be utilized to introduce such deletions or mutations into the subject's endogenous NGAL gene. The engineered cells will express non-functional NGAL polypeptides.

In one embodiment the inhibitor of NGAL activity may consist in an antibody (the term including antibody fragment) that can block NGAL activity.

Antibodies directed against the NGAL can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against NGAL can be prepared and isolated using any technique that provides for the production of antibody molecules by continuous cell lines in culture. Techniques for production and isolation include but are not limited to the hybridoma technique, the human B-cell hybridoma technique and the EBV-hybridoma technique. Alternatively, techniques described for the production of single chain antibodies can be adapted to produce anti-NGAL single chain antibodies. Inhibitor of NGAL activities useful in practicing the present invention also include anti-NGAL antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to NGAL.

Humanized anti-NGAL antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then after raising antibodies directed against the NGAL as above described, the skilled man in the art can easily select those inhibiting NGAL activity.

In another embodiment the Inhibitor of NGAL activity is an aptamer directed against NGAL. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library. The random sequence library is obtainable by combinatorial chemical synthesis of DNA. In this library, each member is a linear oligomer, eventually chemically modified, of a unique sequence. Peptide aptamers consists of a conformationally constrained antibody variable region displayed by a platform protein, such as E. coli Thioredoxin A that are selected from combinatorial libraries by two hybrid methods. Then after raising aptamers directed against the NGAL as above described, the skilled man in the art can easily select those blocking NGAL activity.

In still another embodiment, the Inhibitor of NGAL activity may be a small organic molecule. Typically, the small organic molecule may target the ligand binding site as described in Grzyb J. et al. (Journal of Plant Physiology 163 (2006) 895-915) and Flower D R. et al. (Biochimica et Biophysica Acta 1482 (2000) 9-24) and thus impends the binding between NGAL and its ligands.

An "inhibitor of NGAL expression" refers to a natural or synthetic compound that has a biological effect to inhibit or significantly reduce the expression of the gene encoding for NGAL.

Inhibitors of expression for use in the present invention may be based on anti-sense oligonucleotide constructs. Anti-sense oligonucleotides, including anti-sense RNA molecules and anti-sense DNA molecules, would act to directly block the translation of NGAL mRNA by binding thereto and thus preventing protein translation or increasing mRNA degradation, thus decreasing the level of NGAL, and thus activity, in a cell. For example, antisense oligonucleotides of at least about 15 bases and complementary to unique regions of the mRNA transcript sequence encoding NGAL can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of expression for use in the present invention. NGAL gene expression can be reduced by contacting a subject or cell with a small double stranded RNA (dsRNA), or a vector or construct causing the production of a small double stranded RNA, such that NGAL gene expression is specifically inhibited (i.e. RNA interference or RNAi). Methods for selecting an appropriate dsRNA or dsRNA-encoding vector are well known in the art for genes whose sequence is known. All or part of the phosphodiester bonds of the siRNAs of the invention are advantageously protected. This protection is generally implemented via the chemical route using methods that are known by art. The phosphodiester bonds can be protected, for example, by a thiol or amine functional group or by a phenyl group. The 5'- and/or 3'-ends of the siRNAs of the invention are also advantageously protected, for example, using the technique described above for protecting the phosphodiester bonds. The siRNAs sequences advantageously comprises at least twelve contiguous dinucleotides or their derivatives.

As used herein, the term "siRNA derivatives" with respect to the present nucleic acid sequences refers to a nucleic acid having a percentage of identity of at least 90% with erythropoietin or fragment thereof, preferably of at least 95%, as an example of at least 98%, and more preferably of at least 98%.

As used herein, "percentage of identity" between two nucleic acid sequences, means the percentage of identical nucleic acid, between the two sequences to be compared, obtained with the best alignment of said sequences, this percentage being purely statistical and the differences between these two sequences being randomly spread over the nucleic acid acids sequences. As used herein, "best alignment" or "optimal alignment", means the alignment for which the determined percentage of identity (see below) is the highest. Sequences comparison between two nucleic acids sequences are usually realized by comparing these sequences that have been previously align according to the best alignment; this comparison is realized on segments of comparison in order to identify and compared the local regions of similarity. The best sequences alignment to perform comparison can be realized, beside by a manual way, by using the global homology algorithm developed by SMITH and WATERMAN (Ad. App. Math., vol. 2, p: 482, 1981), by using the local homology algorithm developped by NEDDLEMAN and WUNSCH (J. Mol. Biol., vol. 48, p: 443, 1970), by using the method of similarities developed by PEARSON and LIPMAN (Proc. Natl. Acd. Sci. USA, vol. 85, p: 2444, 1988), by using computer software using such algorithms (GAP, BESTFIT, BLAST P, BLAST N, FASTA, TFASTA in the Wisconsin Genetics software Package, Genetics Computer Group, 575

Science Dr., Madison, Wis. USA), by using the MUSCLE multiple alignment algorithms (Edgar, Robert C., Nucleic Acids Research, vol. 32, p: 1792, 2004). To get the best local alignment, one can preferably used BLAST software. The identity percentage between two sequences of nucleic acids is determined by comparing these two sequences optimally aligned, the nucleic acids sequences being able to comprise additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

shRNAs (short hairpin RNA) can also function as inhibitors of expression for use in the present invention.

Ribozymes can also function as inhibitors of expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of NGAL mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable.

Both antisense oligonucleotides and ribozymes useful as inhibitors of expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and preferably cells expressing NGAL. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated (AAV) viruses, which are double-stranded DNA viruses that have already been approved for human use in gene therapy. Actually 12 different AAV serotypes (AAV1 to 12) are known, each with different tissue tropisms (Wu, Z Mol Ther 2006; 14:316-27). Recombinant AAV are derived from the dependent parvovirus AAV2 (Choi, V W J Virol 2005; 79:6801-07). The adeno-associated virus type 1 to 12 can be engineered to be replication deficient and is capable of infecting a wide range of cell types and species (Wu, Z Mol Ther 2006; 14:316-27). It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a genegun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide, siRNA, shRNA or ribozyme nucleic acid sequence is under the control of a heterologous regulatory region, e.g., a heterologous promoter.

The inhibitor of NGAL activity or expression may be combined with pharmaceutically acceptable excipients, and optionally sustained-release matrices, such as biodegradable polymers, to form therapeutic compositions.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The Inhibitor of NGAL activity or expression of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The inhibitor of NGAL activity or expression of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

The present invention also relates to a method for screening a plurality of candidate compounds for use as a drugs for the prevention and treatment of hypertension comprising the steps consisting of (a) testing each of the candidate compounds for its ability to inhibit NGAL activity or expression and (b) and positively selecting the candidate compounds capable of inhibiting said NGAL activity or expression.

In one embodiment, the method is particularly suitable for screening drugs for reducing chronic vascular inflammation in a patient suffering from hypertension.

Typically, the candidate compound is selected from the group consisting of small organic molecules, peptides, polypeptides or oligonucleotides. Other potential candidate compounds include antisense molecules, siRNAs, or ribozymes.

Testing whether a candidate compound can inhibit NGAL activity or expression can be determined using or routinely modifying assays known in the art. For example, the method may involve contacting cells expressing NGAL with the candidate compound, and measuring the NGAL mediated activity, and comparing the cellular response to a standard cellular response. Typically, the standard cellular response is measured in absence of the candidate compound. A decrease cellular response over the standard indicates that the candidate compound is an inhibitor of NGAL activity. In another embodiment the invention provides a method for identifying a ligand which binds specifically to NGAL. For example, a cellular compartment, such as a membrane or a preparation thereof, may be prepared from a cell that expresses a molecule that binds NGAL. The preparation is incubated with labelled NGAL and complexes of ligand bound to NGAL are isolated and characterized according to routine methods known in the art. Alternatively, the NGAL interacting polypeptide may be bound to a solid support so that binding molecules solubilized from cells are bound to the column and then eluted and characterized according to routine methods. In another embodiment, a cellular compartment may be prepared from a cell that expresses a molecule that binds NGAL such as a molecule of a signalling or regulatory pathway modulated by NGAL. The preparation is incubated with labelled NGAL in the absence or the presence of a candidate compound. The ability of the candidate compound to bind the binding molecule is reflected in decreased binding of the labelled ligand.

The candidate compounds that have been positively selected may be subjected to further selection steps in view of further assaying its properties on hypertension. For example, the candidate compounds that have been positively selected may be subjected to further selection steps in view of further assaying its properties on animal models for hypertension. Typically, the positively selected candidate compound may be administered to the animal model and the blood pressure is determined and compared with the blood pressure in an animal model that was not administered with the candidate compound.

The invention will be further illustrated by the following figures and examples. However, these examples and figures should not be interpreted in any way as limiting the scope of the present invention.

FIGURES

FIG. 1: Similar effects of NGAL knock-down with NGAL siRNA (panels A-C) or gene inactivation (Knock-out) (panels B-D) on vasoreactive response to phenylephrine in aorta and blood pressure.

Figure 2A:
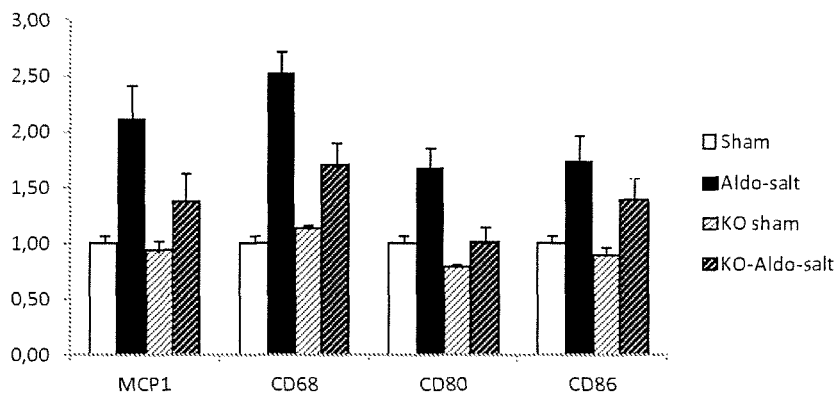
Figure 2B:
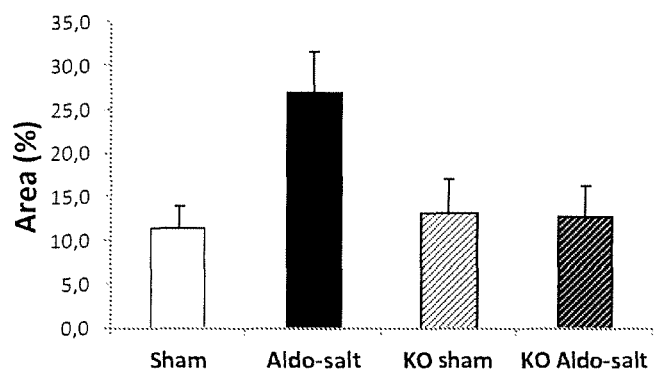

FIG. 2. Upon aldo-salt challenge, NGAL inactivation (NGAL KO mice) blunts the increase of mRNA expression of inflammatory markers (MCP1, CD68, CD80, CD86) in the heart (panel A) as well as osteopontin, a marker of inflammation in the aorta (panel B). The Increase in plasma C Reactive Protein (panel C) induced by aldo-salt challenge is also blunted in NGAL KO mice. Sham: control mice, Aldo-salt: nephrectomy aldo salt treatment, KO: NGAL knockout mice. mean±SEM, n=6-8; *p<0.05, p<0.01, *p<0.001

FIG. 3. NGAL is an aldo/MR target in DCs (A) and macrophages (B). A:DCs were obtained from male SD rat bone marrow stem cells and differentiated during 6 days with GM-CSF. DCs were incubated with aldo (10 nM), spironolactone (5 µM), aldo plus spironolactone, or vehicle for 24 hr. *p<0.05 by ANOVA analysis (n=4); B: peritoneal macrophages from WT mice were stimulated or not with aldo (10 nM+/−RU28318 (MR antagonist). NGAL behaves similarly as MCP1 (monocy chemoattractant protein).

EXAMPLE 1

Material & Methods

Mouse Models with NGAL Gene Inactivation or NGAL siRNA Infusion

For vascular reactivity analyses, 400 microgram/Kg/day siRNA directed against NGAL in sterile 9‰NaCl was administered by subcutaneous ALZET® 1004 osmotic mini pumps for 3 weeks in C57/bl6 wild-type mice compared to wild-type mice infused with solvent only.

For blood pressure analyzes, Aldosterone-treated mice (nephrectomy/Aldo/salt) received 200 µg/kg BW/day Aldo, delivered subcutaneously via ALZET® osmotic mini pumps (Charles River Laboratories, L'Arbresle, France) with 1% sodium chloride to drink for 5 weeks. The control mice were uninephrectomized and maintained on standard chow and water. Mice undergoing unilateral nephrectomy/aldo/salt treatment are referred to as NAS mice and vehicle-infused mice are referred to as Sham mice. Control or NGAL KO mice (9 weeks old, on C57B16 background, kindly provided by Tak W. Mak, Toronto, Canada) were treated with NAS. C57/bl6 wild type mice were treated with NAS with or without siRNA infusion (400 microgram/Kg/day in sterile 9‰ NaCl was administered by subcutaneous ALZET® 2006 osmotic mini pumps for 5 weeks).

Ex Vivo Vascular Reactivity of Isolated Arteries

Vascular contractility and dilation were assessed in infrarenal aortic segments. Abdominal aortas, mounted in a Mulvany-Halpern myograph (Danish Myo Technology), were first allowed to stabilize for at least 40 minutes and were then stimulated with 60 mmol/l KCl. Endothelial integrity was assessed by evaluating the vasodilator effect of $10^{-6}$ mol/l acetylcholine (Ach, Sigma-Aldrich), after preconstriction treatment with $10^{-6}$ mol/l phenylephrine (Phe, Sigma-Aldrich). Cumulative dose-response curves for Phe were then plotted.

Blood Pressure Measurement in Conscious Mice

Systolic blood pressure (SBP) was measured after 3 days training in trained conscious mice by tail cuff plethysmography, with a BP2000 Visitech device (Bioseb) as recommended by the supplier.

Results

Figure 1B:
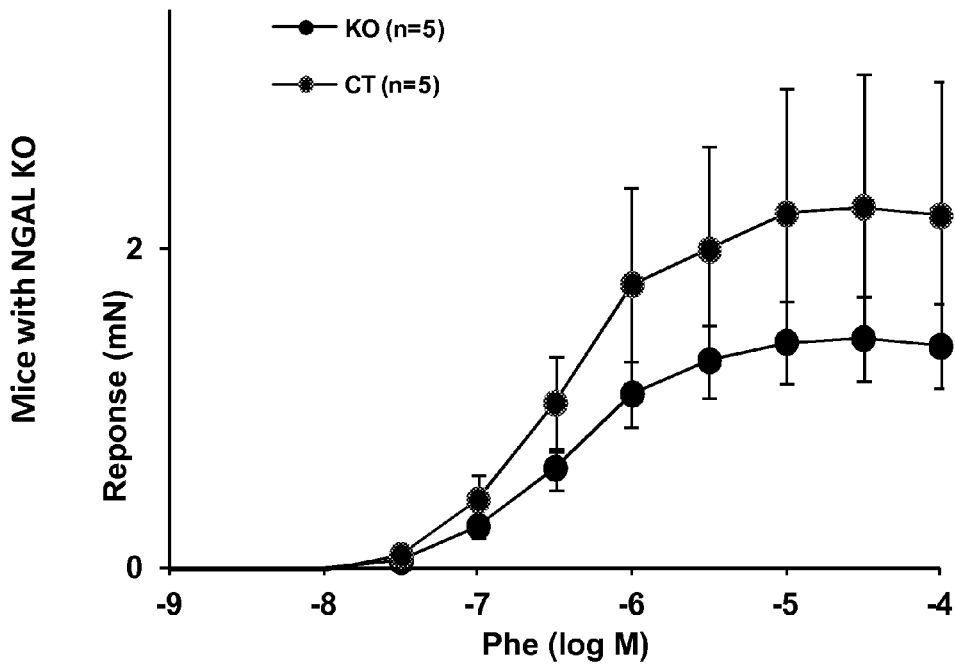
Figure 1C:
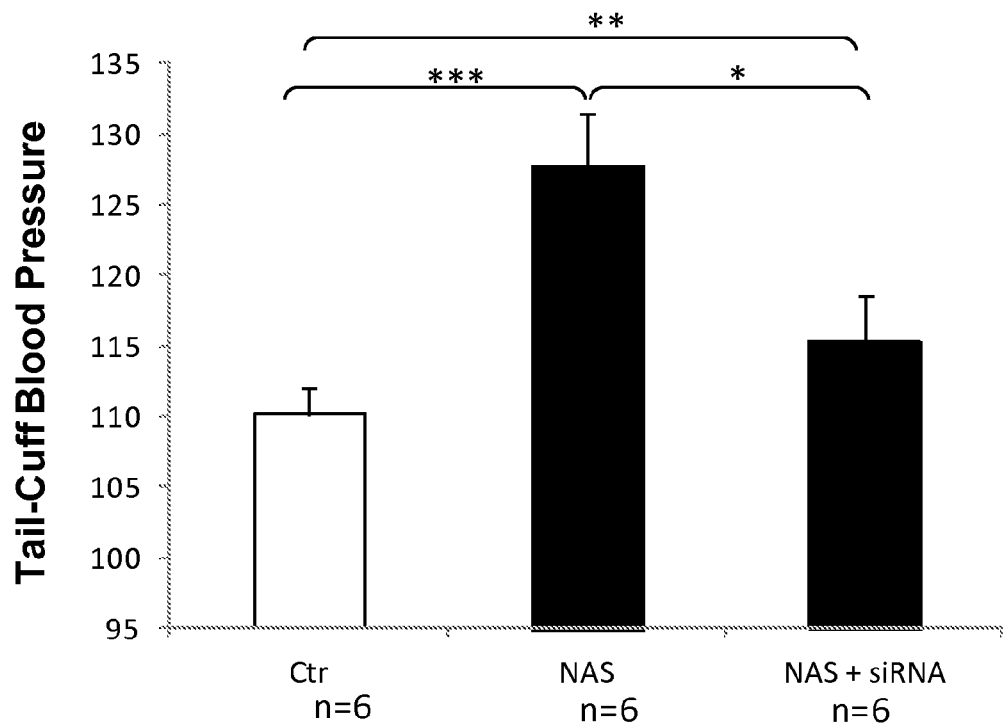
Figure 1D:
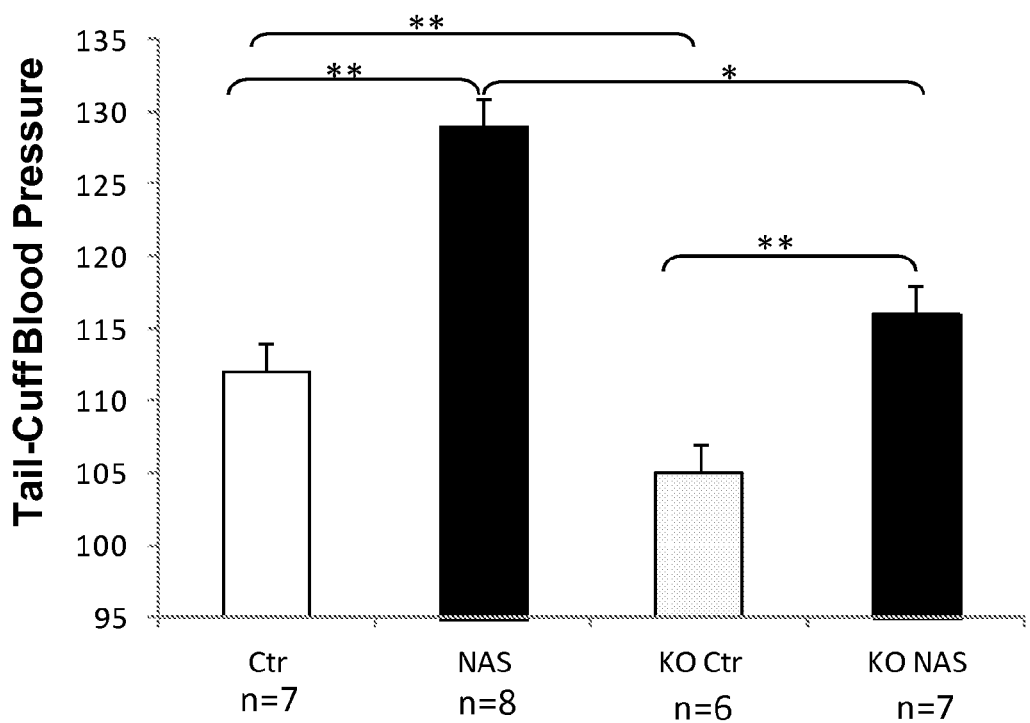

FIGS. 1A and 1B show the effect on vascular reactivity and vasoconstrictive response to increasing concentration of Phe. Knock-down (siRNA) or absence (KO) of NGAL expression resulted in decreased vasoconstrictive aortic response to increasing concentration of Phe in a similar way without changes in Phe sensitivity (ED50). FIGS. 1C and 1D show the effect on blood pressure response to NAS treatment. Knock-down (NAS+siRNA) or absence of NGAL (KO NAS) expression resulted to similar blunting of the increased blood pressure response to NAS treatment (NAS versus sham).

EXAMPLE 2

Methods

Macrophages are purified from abdominal cavity from mice, after 4 days of inflammation induced by thioglycollate injection. Dendritic cells are obtained after 7 days of incubation of bone marrow precursors cells (from mice bone marrow) with GM-CSF (granulocyte macrophage colony-stimulating factor).

Results:

Low-grade inflammation has a pathological role in cardiovascular disease and inflammatory biomarkers (C-Reactive Protein, cytokines and their receptors) associated with poor clinical outcomes and prognosis (1, 2). Patients with hypertension present a chronic vascular inflammatory state that may imply adaptive immune response mechanisms (1, 2). In the aldosterone field, it has been recognized that vascular inflammation and the infiltration of the arterial wall and perivascular space by immune cells is an early event observed after inappropriate MR-activation (3, 4). Monocyte/macrophage deficiency in osteopetrotic mice results in absence of aldosterone-induced oxidative stress and endothelial dysfunction, indicating a major role of macrophages in this process (5). T regulatory cells (Treg) prevent aldosterone-induced vascular injury in mice (4) (6,7). The MR is present in immune cells, as dendritic cells (DCs) (6, 7), and macrophages, and pharmacological MR blockade correlates with prevention/improvement of the chronic inflammatory state that associates with CV dysfunction due to inadequate MR activity (6, 7). Macrophages also participate to the hypertensive and remodeling effect of aldo-salt, as shown in macrophage-specific MR KO mice (8). Taken together, these data suggest that aldo/MR modulates innate and adaptive immunity, that may have a critical role in initiating/maintaining vascular remodeling, as well as hypertension, in response to exogenous aldosterone and/or MR activation.

Figure 2C:
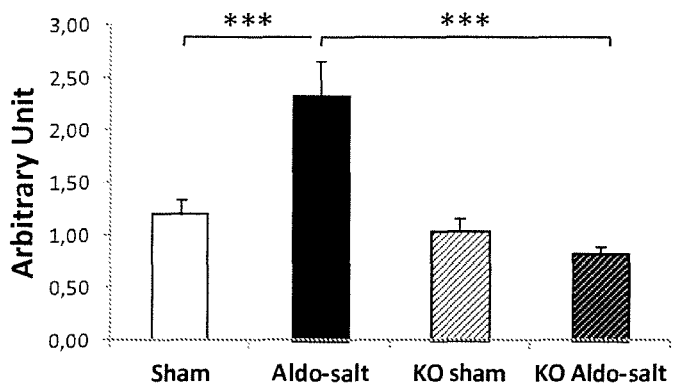
Figure 3A:
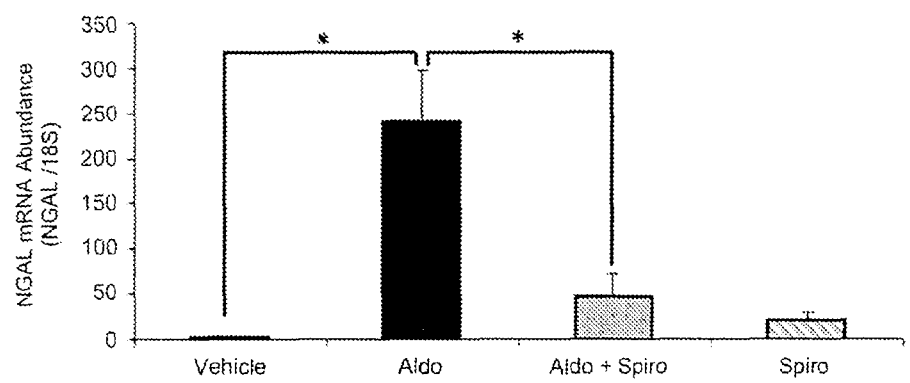
Figure 3B:
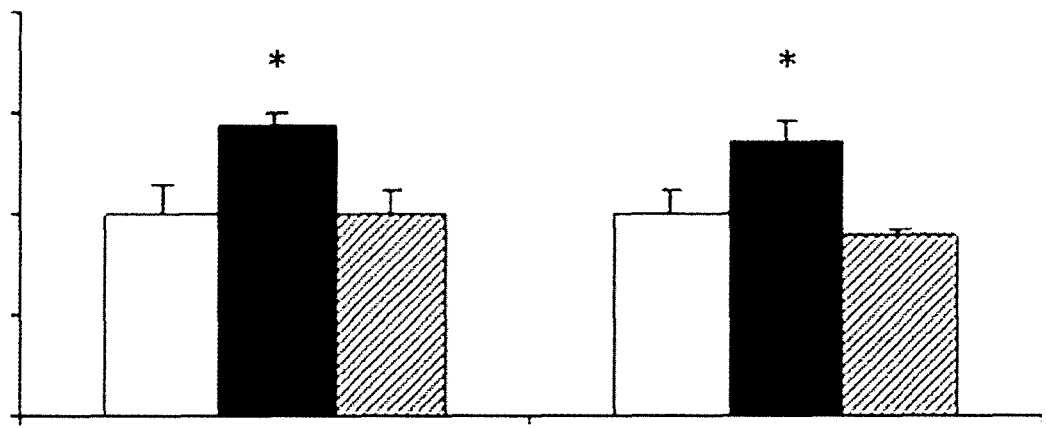

We used NGAL knock-out mice to analyze the role of NGAL in this process. NGAL inactivation prevents the aldosterone-salt induced hypertension (see EXAMPLE 1). Our results indicate that NGAL plays a role in inflammation and may explain the role of NGAL in aldo-salt induced high blood pressure. NGAL gene inactivation blunts the increase in inflammatory markers in the heart (FIG. 2A), as well as aldo-induced increase of osteopontin an inflammatory marker in the aorta (FIG. 2B)/Moreover NGAL gene inactivation prevents global inflammation as shown by the prevention of increased in C-Reactive Protein plasma levels (FIG. 2C). Data obtained ex vivo demonstrated that NGAL is expressed in dendritic cells and is upregulated by aldo via MR activation (ie blocked by the MR antagonist spironolactone) (FIG. 3A). Moreover, NGAL is also an aldo/MR target gene in the macrophages (FIG. 3B). Therefore NGAL is a mediator of aldo/MR-mediated recruitment and/or activation of inflammatory cells which in turn is responsible for hypertension and extracellular matrix remodeling in the cardiovascular system.

1. Schiffrin E L. Immune modulation of resistance artery remodelling. Basic & clinical pharmacology & toxicology. 2012; 110(1):70-
2. Schiffrin E L. The Immune System: Role in Hypertension. Can J Cardiol. 2012. Epub 2012 Sep. 21.
3. Kasal D A, Schiffrin E L. Angiotensin II, Aldosterone, and Anti-Inflammatory Lymphocytes: Interplay and Therapeutic Opportunities. International journal of hypertension. 2012; 2012:829786. Epub 2012 Jun. 12.
4. Kasal D A, Barhoumi T, Li M W, Yamamoto N, Zdanovich E, Rehman A, et al. T regulatory lymphocytes prevent aldosterone-induced vascular injury. Hypertension. 2012; 59(2):324-30. Epub 2011 Dec. 8.
5. De Ciuceis C, Amiri F, Brassard P, Endemann D H, Touyz R M, Schiffrin E L. Reduced vascular remodeling, endothelial dysfunction, and oxidative stress in resistance arteries of angiotensin II-infused macrophage colony-stimulating factor-deficient mice: evidence for a role in inflammation in angiotensin-induced vascular injury. Arterioscler Thromb Vasc Biol. 2005; 25(10):2106-13. 16. Herrada A A, Campino C, Amador C A, Michea L F, Fardella C E, Kalergis A M. Aldosterone as a modulator of immunity: implications in the organ damage. J Hypertens. 2011; 29(9):1684-92. Epub 2011 Aug. 10.
6. Herrada A A, Contreras F J, Marini N P, Amador C A, Gonzalez P A, Cortes C M, et al. Aldosterone promotes autoimmune damage by enhancing Th17-mediated immunity. J Immunol. 2010; 184(1):191-202. Epub 2009 Dec. 2.
7. Rickard A J, Young M J. Corticosteroid receptors, macrophages and cardiovascular disease. Journal of molecular endocrinology. 2009; 42(6):449-59. Epub 2009 Jan. 23.
8. Rickard A J, Young M J. Corticosteroid receptors, macrophages and cardiovascular disease. Journal of molecular endocrinology. 2009; 42(6):449-59. Epub 2009 Jan. 23.

REFERENCES

Throughout this application, various references describe the state of the art to which this invention pertains. The disclosures of these references are hereby incorporated by reference into the present disclosure.

The invention claimed is:
1. A method for treating hypertension in a subject in need thereof, comprising administering to said subject an inhibitor of Neutrophil Gelatinase-Associated Lipocalin (NGAL) gene expression, wherein the subject is a non obese subject.
2. The method according to claim 1 wherein the inhibitor is a siRNA.
3. The method according to claim 1, wherein the inhibitor is selected from the Group consisting of siRNA, shRNA, anti-sense oligonucleotides and ribozymes.

* * * * *